US009655595B2

(12) United States Patent
Glossop et al.

(10) Patent No.: US 9,655,595 B2
(45) Date of Patent: May 23, 2017

(54) SYSTEM, METHOD AND DEVICE FOR PROSTATE DIAGNOSIS AND INTERVENTION

(71) Applicants: Arcitrax Inc., Toronto (CA); The United States of America, as represented by the Secretary, Department of Health and Human Services, Washington, DC (US)

(72) Inventors: Neil Glossop, Toronto (CA); Bradford Wood, North Bethesda, MD (US)

(73) Assignees: Arcitrax Inc., Ontario (CA); The United States of America, as represented by the Secretary, Dept. of Health and Human Services, Washington, DC (US)

( * ) Notice: Subject to any disclaimer, the term of this patent is extended or adjusted under 35 U.S.C. 154(b) by 0 days.

(21) Appl. No.: 13/918,413

(22) Filed: Jun. 14, 2013

(65) Prior Publication Data

US 2013/0338477 A1    Dec. 19, 2013

Related U.S. Application Data

(60) Provisional application No. 61/659,730, filed on Jun. 14, 2012, provisional application No. 61/776,293, filed on Mar. 11, 2013.

(51) Int. Cl.
*A61B 10/02*    (2006.01)
*A61B 5/00*    (2006.01)
(Continued)

(52) U.S. Cl.
CPC ........ *A61B 10/0241* (2013.01); *A61B 5/4887* (2013.01); *A61B 17/3403* (2013.01);
(Continued)

(58) Field of Classification Search
CPC ............ A61B 10/0241; A61B 10/0275; A61B 17/3403; A61B 19/5225; A61B 19/5244;
(Continued)

(56) References Cited

U.S. PATENT DOCUMENTS

| 6,095,981 A * | 8/2000 | McGahan | ............ A61B 8/0833 600/461 |
| 2008/0171940 A1* | 7/2008 | McGahan | .......... A61B 17/3403 600/461 |

(Continued)

OTHER PUBLICATIONS

Lindseth, F., et al., "Probe Calibration for Freehand 3-D Ultrasound", Ultrasound in Medicine and Biology, 29(11): 1607-1623, Nov. 2003.
(Continued)

*Primary Examiner* — Michael Rozanski
(74) *Attorney, Agent, or Firm* — Sheppard Mullin Richter & Hampton LLP

(57) ABSTRACT

Methods, systems, and devices for assisting or performing an image-guided prostate procedure are disclosed. A needle assembly includes a needle guide, a needle device, a position sensor and additional features. The position sensor allows for the tracking of the needle assembly. A method for performing image-guided prostate procedures includes pre-operative procedures and intra-operative procedures. The pre-operative procedures include imaging studies to model the prostate and identify targets. The pre-operative procedures models are used during a prostate procedure to track the target and the devices used for the procedure. A system for performing image-guided procedures includes the needle assembly and other components.

24 Claims, 13 Drawing Sheets

(51) Int. Cl.
*A61B 17/34* (2006.01)
*A61B 17/00* (2006.01)
*A61B 5/01* (2006.01)
*A61B 5/06* (2006.01)
*A61B 34/20* (2016.01)
*A61B 90/00* (2016.01)

(52) U.S. Cl.
CPC ............... *A61B 5/01* (2013.01); *A61B 5/066* (2013.01); *A61B 10/0275* (2013.01); *A61B 34/20* (2016.02); *A61B 90/37* (2016.02); *A61B 2017/00092* (2013.01); *A61B 2017/00274* (2013.01); *A61B 2017/3413* (2013.01); *A61B 2034/2051* (2016.02); *A61B 2090/365* (2016.02)

(58) Field of Classification Search
CPC  A61B 2017/00092; A61B 2017/00274; A61B 2017/3413; A61B 2019/5251; A61B 2019/5291; A61B 5/01; A61B 5/066; A61B 5/4887
See application file for complete search history.

(56) References Cited

U.S. PATENT DOCUMENTS

| | | | |
|---|---|---|---|
| 2009/0030339 A1* | 1/2009 | Cheng et al. | 600/562 |
| 2010/0041996 A1 | 2/2010 | Nygaard et al. | 600/459 |
| 2011/0087096 A1* | 4/2011 | Behar | 600/438 |
| 2011/0224576 A1* | 9/2011 | Jackson et al. | 600/567 |
| 2013/0090554 A1* | 4/2013 | Zvuloni et al. | 600/424 |
| 2015/0045648 A1* | 2/2015 | Pasternak et al. | 600/409 |

OTHER PUBLICATIONS

Gee, A. H., et al., "3D Ultrasound Probe Calibration Without a Position Sensor", CUED/F-INFENG/TR 488,Cambridge University, Department of Engineering, Sep. 2004, pp. 1-20.

Shams, R., et al., "Real-Time Simulation of Medical Ultrasound from CT Images", MICCAI 2008, Part II, LNCS 5242, 2008, pp. 734-741.

* cited by examiner

SYSTEM, METHOD AND DEVICE FOR PROSTATE DIAGNOSIS AND INTERVENTION

This application claims priority to provisional patent application Ser. No. 61/659,730 filed Jun. 14, 2012, and to provisional patent application Ser. No. 61/776,293 filed Mar. 11, 2013, the disclosures of each of which are incorporated by reference herein in their entireties.

STATEMENT OF GOVERNMENT RIGHTS

The Government of the United States of America may have certain rights in the invention disclosed and claimed below.

FIELD OF INVENTION

Embodiments of the invention relate to methods, systems, and devices for assisting or performing an image-guided prostate biopsy or therapy.

BACKGROUND

Prostate cancer is second only to lung cancer as a leading cause of cancer death in men in the United States, where one out of every six men are affected by the disease during their lifetime. Currently, prostate cancer is screened using serum prostate-specific antigen (PSA) screening. As the test is presently unreliable, patients who are deemed at risk undergo biopsy under real-time 2D transrectal ultrasound (TRUS) guidance. Because potential cancer cells are almost always indistinguishable from normal prostate tissue under ultrasound, the procedure is performed in a systematic but random manner over the entire gland. During "sextant biopsy", the most common form of TRUS biopsy and current standard of care, one or more biopsies are obtained from each of six zones that the prostate is divided into and analyzed.

Sextant biopsy is widely used due to its low cost and simplicity relative to other methods of detecting prostate cancer but has been shown to have a significant false negative rate, which has been shown to be higher for lesions located in the anterior or apical prostate. The results of sextant biopsy are commonly reported in text format alone, or at best, using a crude rough standard map of the prostate on which biopsy results are manually annotated by the pathologist.

In some cases, cancers may be seen under one or more volumetric imaging methods or sequences such as Magnetic Resonance Imaging (MRI), diffusion weighted imaging, dynamic contrast enhanced MRI, MR spectroscopy, or other volumetric data scanning (ultrasound elastography, ultrasound thermometry, or spectrum analysis of raw radiofrequency signal from ultrasound transducer). Regression analysis of multi-parametric imaging volumetric data weighs each imaging parameter and assigns a relative risk value to each image or data type in order to assign a total risk for each voxel (roughly between 100 microns and 5 mm). Voxel analysis may be performed on voxels of different sizes or by re-sampling based upon borrowed features from neighboring voxels, or upon any algorithm that weighs the various MRI sequences and raw radiofrequency ultrasound signal to assign a risk for cancer to each voxel. The spectrum of the raw ultrasound signal is then analyzed, and referenced to a library or look-up table for cancer risk at any voxel location (which are based upon prior RF signal or imaging to tissue correlation). In these cases, it is desirable to sample the lesion seen on MRI using biopsy to confirm the existence of and evaluate the type of cancer. The result of the biopsy may then alter treatment decisions. The current state of the art does not allow easy targeting of a biopsy needle into a potential cancer site seen under MRI once the patient has been moved out of the MRI. While possible to perform the intervention in the MRI magnet itself, this is time consuming and costly.

In addition, it is sometimes desirable to perform minimally invasive, nerve sparing or organ preserving therapy on the prostate using techniques such as cryotherapy or laser ablation that preserve at least part of the prostate and thereby minimize the chance of severe complications that sometimes accompany surgery to remove the entire gland. By precisely targeting focal cancer lesions, surgery that spares the gland for at least the short term, may be possible. Additionally, in low dose brachytherapy, it would be ideal if radioactive seeds placed in the prostate can be clustered in the area where most of the lesions are found. All of these treatment modalities are typically used for localized and image-able prostate cancer, typically on patients who might otherwise undergo "active surveillance" or "watchful waiting" for a slow growing and photogenic prostate cancer, such as cases where the Gleason score is less than 7.

Image guided procedures are well known in the art and use a position sensor such as an optical or electromagnetic tracking system to determine the location and orientation of an instrument such as a biopsy probe or of an imaging device such as a hand-held ultrasound probe or fluoroscopy device, CT fluoroscopic scanner gantry, etc. in a coordinate system. When performing an image guided biopsy it is sometimes important to record the geometric location and orientation of the imaging device if used, and the biopsy device (as determined by the position sensor). It may also be helpful to capture a video image or several images from the imaging device at the time the biopsy is taken. This enables recording of the precise origin of a biopsy which is especially important in cases where the target is small. By knowing the position of an abnormal sample, it may be possible to target treatment to the abnormal tissue, or conversely, to spare healthy tissue.

Current biopsy devices lack an integrated electronic sensor, such as an electrical switch, that can be used by software associated with the position sensor to determine the precise instant at which the biopsy is taken. This makes it difficult to record an image and position data at the exact time of biopsy, since no electronic trigger is available. Instead, paper or verbal notes may be taken or a video/data recording may be taken by the imaging system to capture a plurality of sequential video frames. Of the many hundreds of frames that are captured in just a few seconds, only one or two may show the actual biopsy being performed with the rest being of little value. It is therefore difficult and time consuming, and may involve complicated video image analysis software to obtain the video location of the biopsy. Once the correct video frame has been located it then is necessary to correlate the position sensor data taken at the same time as the video to locate the same time point in the data stream. Only then is it possible to obtain the quantitative position and orientation data of the biopsy. This too may be time consuming or involve collection and processing of a large amount of data.

A signal at the time of biopsy may be obtained by using a switch within the biopsy probe. However, this may be costly and complicated to implement given that the biopsy probe is typically an inexpensive mechanical device and does not normally contain electronics. Such a switch also is not required for many simple biopsies that do not involve computer assisted image guided surgery, and would only add to the cost of the device.

With regards to performing prostate therapies, the current state of the art uses a transperineal approach in which a plate contains a plurality of holes into which needles are inserted. The needles may contain radioactive seeds for use in brachytherapy, cryogenically cooled probes, or thermal therapy probes in which heat is applied to all or portions of the prostate in order to ablate or otherwise treat the organ. The needle may be placed using guidance from imaging modalities such as transrectal ultrasound, intraoperative MRI fused MR/US, PET/CT or other modalities or combination thereof. In some cases it is preferable to perform the therapy using a transrectal needle approach rather than a transperineal method. In these cases a needle may be inserted using an imaging modality such as an MRI scanner or a transrectal ultrasound (TRUS) probe to help guide the needle.

Numerous TRUS needle guides are available, such as those manufactured by Civco Inc. (Kalowna, Iowa), for example the "613-246 Sterile endocavity needle guide for Philips C9-5ec transducer". This class of device is removably attached to the TRUS transducer and houses a tube or channel into which a biopsy or other needle may be inserted. The orientation and position of the needle guides of the same type remains repeatable each time it is re-attached to the transducer.

The channel and thus the needle path has a fixed orientation relative to the scan plane of the transducer, enabling the ultrasound supplier to "predict" the path of the needle and apply an overlayed graphic line to the anatomical image from the ultrasound to help guide the needle to the correct location. This line represents the needle path if it were to be extended. Furthermore, the needle channel is placed directly in the field of view of the imaging array of the transducer, so that the needle can be directly viewed as it is extended out of the needle guide.

Current ultrasound needle guides are sufficient to perform transrectal biopsies but are not designed for transrectally applied therapy. In performing therapy, there may be advantages to inserting a treatment needle transrectally instead of through the perineum. These include the application of the therapy using a well-established workflow that closely follows that of prostate biopsy. In these cases, the needle is inserted through the rectal wall and the therapy applied. During application of the therapy, it is critical to be able to visualize and image all aspects of the gland.

In a prior art needle guide, a biopsy needle 104 is placed through a needle guide 100 such as shown in FIG. 1. Needle guide 100 contains a housing 101, that may be removably attached to an ultrasound transducer such as a TRUS transducer (not shown). Needle guide 100 also contains a tube 102 into which a functional needle such as a biopsy needle 104 is inserted. In this prior art needle guide, biopsy needle 104 is slideably and axially constrained to tube 102, i.e. biopsy needle 104 may only be slid up and down tube 102 or axially rotated along its length. Once a needle is inserted into tube 102 and exits the end hole 103, and into tissue 105, the transducer that is also attached to the needle guide may not be reoriented (except for an axial spin as note above) or repositioned to better visualize the therapy without removing the needle from the tissue. Thus, the ultrasound probe must remain in place while the therapy is applied. If the action of the therapy cannot be directly and completely viewed by the ultrasound transducer in this position, the therapy cannot be properly monitored. With the needle in place the transducer is effectively "pinned" to a location and may not be freely moved to view the progress and extent of the therapy.

Furthermore, it may be necessary to place more than one functional needle to effectively apply the therapy, for example in Irreversible Electroporation (IRE), multi-pole radiofrequency ablation, cryotherapy etc. Again the prior art does not allow this to be performed. It may also be necessary to use additional functional needles to effectively monitor the therapy, e.g. thermal sensors such as thermocouples. Again, prior art does not allow for this possibility.

In these cases, it is highly desirable to disengage one or more needles from the TRUS probe after placement, allowing for better monitoring of the needle's location, subsequent therapy and/or to allow the positioning and placement of subsequent needles.

Accordingly there exists a need to solve these and other problems to facilitate minimally invasive needle procedures in the prostate. For example, there is a need to facilitate minimally invasive transrectally applied needle procedures in the prostate while allowing the physician to move and reorient a transducer. There is also a need to facilitate the placement of devices at specific targets as determined using MRI, Positron Emission Tomography (PET), Computed Tomography (CT) or other volumetric scan techniques, but with the assistance of low cost and convenient imaging systems such as TRUS. There is also a need to facilitate the collection of data during image guided procedures and treatments.

SUMMARY

Embodiments described herein solve these and other problems by providing methods, systems and devices for image-guided prostate procedures. In a first aspect, a needle assembly is disclosed. In one embodiment, the needle assembly includes a needle guide, a needle device, and a position sensor. The needle guide may contain one or more lumens to facilitate insertion of needles, cannulas, thermocouples, thermal and cryogenic ablation devices, catheters, or other instruments.

In some embodiments, the needle guide may include one or more position indicating elements that may provide tracking device space data regarding the position and orientation of the needle guide. In other embodiments, the position indicating elements may provide the location and/or orientation of one or more cannulas, needles, catheters, and/or instruments inserted into lumens in the needle guide.

In some embodiments the needle guide may include devices for warming or cooling tissue adjacent to the needle guide to facilitate thermal procedures. The needle guide may include temperature measurement devices. In another embodiment, the needle device is a spring loaded biopsy needle. In some embodiments, the needle guide may include a microphone, an accelerometer, or a vibration detector. In some embodiments, the needle guide may include a plurality of tubes exiting the guide at different locations and orientations.

In a second aspect, a method for performing image-guided prostate procedures is disclosed. In one embodiment, the method includes pre-operative procedures and intra-operative procedures.

In one embodiment, the pre-operative procedures include performing a volumetric imaging study on a prostate of a patient, segmenting the volumetric imaging study to produce an outline, mesh, or solid model of the prostate, co-registering an image from the volumetric imaging study with a reference image, identifying a target on the image from the volumetric imaging study, and transposing the target on the reference image.

In one embodiment, the intra-operative procedures include inserting a probe into the patient, scanning the prostate of the patient with the probe, matching a cross sectional slice of an image from the patient scan to the image from the volumetric imaging study, and superimposing the target on the image from the volumetric imaging study onto images from the patient scan.

In a third aspect, a system for performing image-guided prostate procedures is disclosed. In one embodiment, the system may include a computer element, a tracking device, an imaging device, an imaging device tracker, a needle assembly, or other elements.

In an embodiment, the tracking device may be used to determine the location and trajectory of a puncture needle, a treatment needle, and a TRUS probe. In another embodiment, the tracking device may be used to obtain data regarding the three-dimensional location, position, coordinates, or other information regarding one or more position indicating elements within or around an anatomical region of a patient.

In some embodiments, the imaging device may include a previously acquired image such as images obtained using magnetic resonance imaging, computed tomography, cone beam CT, positron emission tomography, ultrasound, ultrasound elastography, x-ray, magnetic particle imaging, etc. In some embodiments the imaging device may include a live imaging device such as an ultrasound, fluoroscopic x-ray or endoscope such as a cystoscope, or a photonic needle for tissue characterization, such as might be accomplished with polarized backscatter signal analysis to estimate chromatin density or nuclear size.

In another embodiment, the live imaging modality may include a tracker to enables its position and orientation to be determined. The tracker may be embedded to, attached, or embedded in the imaging device.

In some embodiments, the tracking device or position sensor may be operatively connected to the computer element via an input/output or otherwise send and receive data to and from the computer element. In some embodiments, the tracking device may include an electromagnetic (EM) tracking device, global positioning system (GPS) enabled tracking device, an ultrasonic tracking device, a fiber-optic tracking device, an optical tracking device, radar tracking device, or other type of tracking device.

The various objects, features, and advantages of the invention will be apparent through the detailed description and the drawings attached hereto. It is also to be understood that the following detailed description is exemplary and not restrictive of the scope of the invention.

DETAILED DESCRIPTION

Figure 1:
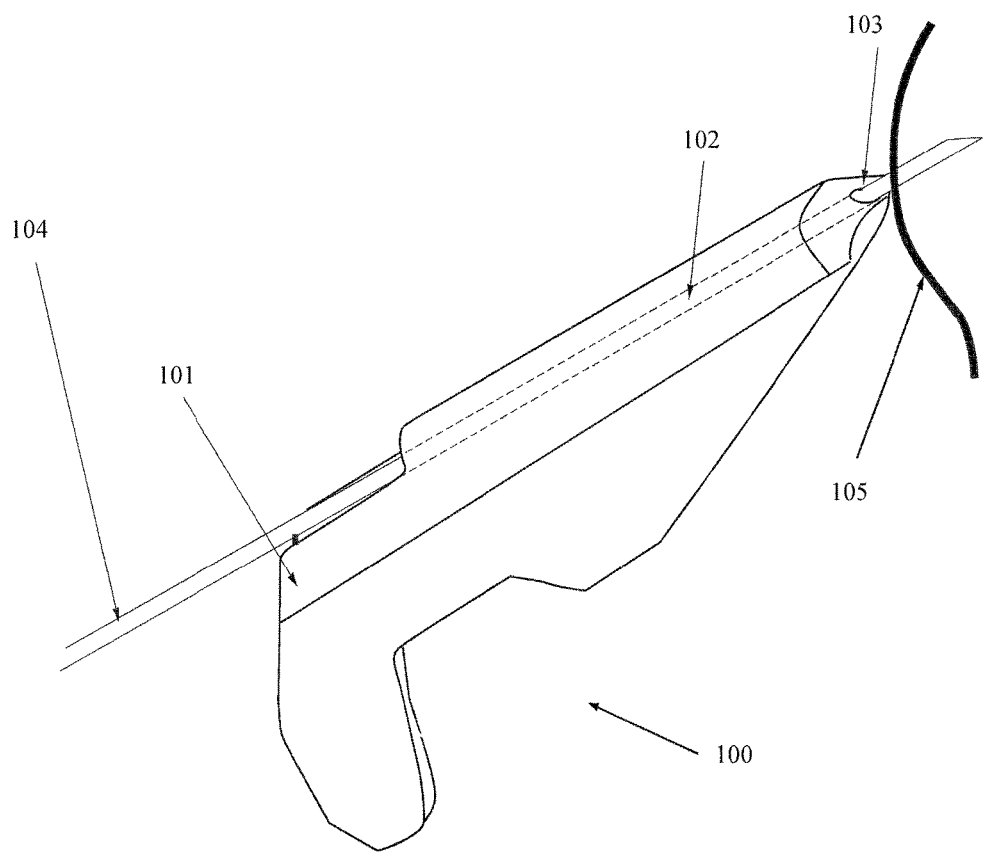
FIG. 1 is a perspective view of a prior art needle guide.
Figure 2:
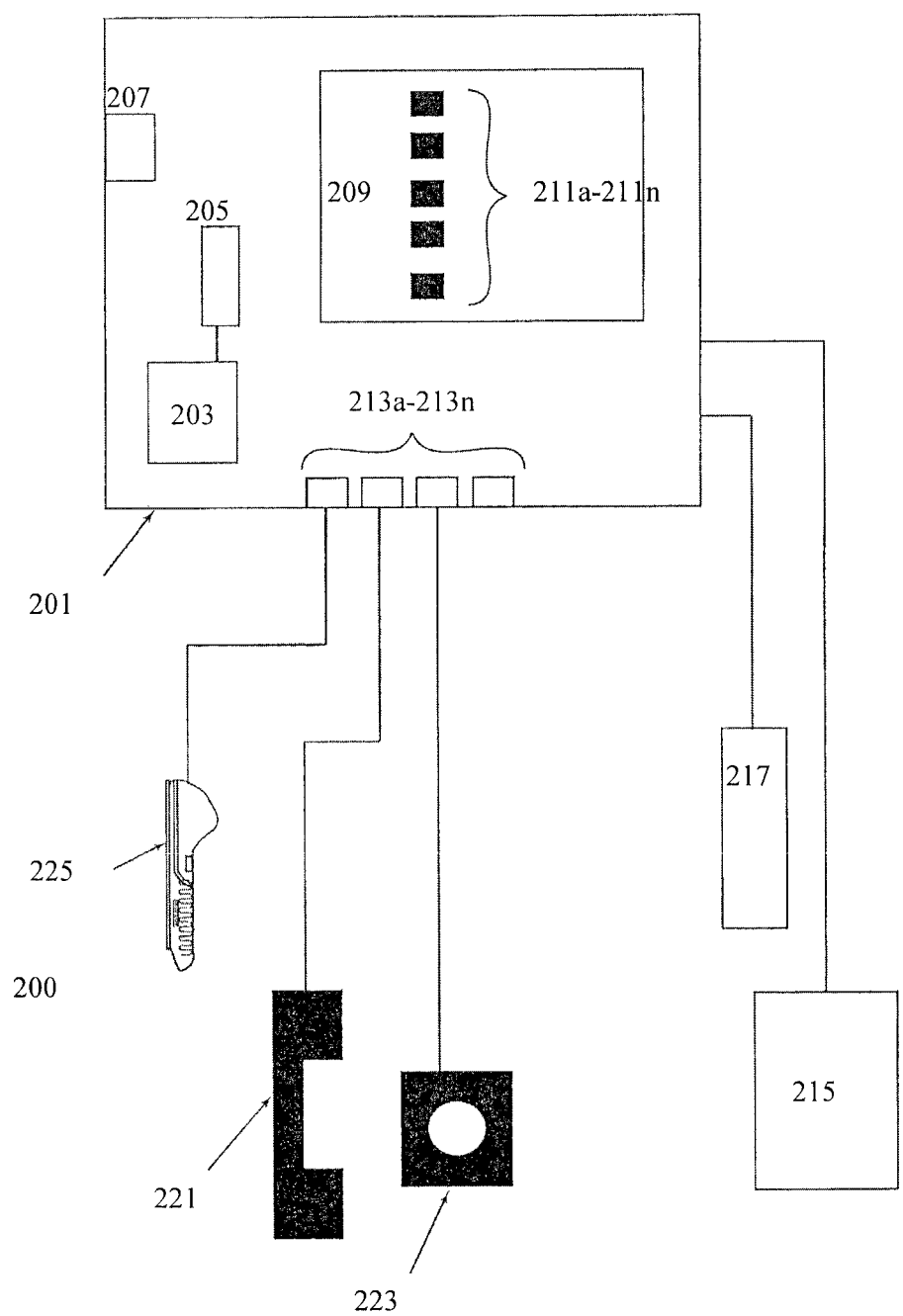
FIG. 2 is a schematic view of a system for assisting or performing image-guided prostate procedures.

Embodiments as described herein provide devices, systems, and methods for assisting or performing image-guided prostate procedures. Image-guided prostate procedures may include biopsies or focal ablation of the prostate. FIG. 2 illustrates a system 200 for assisting or performing image-guided prostate procedures. System 200 may include a computer element 201, a tracking device 221, an imaging device 223, a needle assembly 225, or other elements.

Computer element 201 may include a processor 203, a memory device 205, a power source 207, a control application 209, one or more software modules 211a-211n, one or more inputs/outputs 213a-213n, a display device 215, a user input device 217, and other elements. In some embodiments, the processor 203 may be configured to perform the features and functions of the invention as described herein. Memory device 205 or other memory or data storage elements or methods may store data or otherwise provide instructions to the processor 203.

Computer element 201 may be or include one or more servers, personal computers, laptop computers, mobile computers, tablet computers, or other computer devices. Computer element 201 may receive, send, store, or manipulate data necessary to perform any of the processes, calculations, image formatting, image display, or other operations described herein. Computer element 201 may also perform any processes, calculations, or operations necessary for the function of the devices, elements, instruments, or apparatus described herein.

In some embodiments, computer element 201 may host a control application 209. Control application 209 may comprise a computer application which enables one or more software modules 211a-211n. Software modules 211a-211n may enable processor 203 to receive (e.g., via a data reception module), send, or manipulate data regarding the anatomy of a patient, one or more objects, or other data. This data may be stored in memory device 205 or other data storage location. In some embodiments, software modules 211a-211n enables processor 203 to receive live or stored data (e.g., via the data reception module), send, or manipulate data regarding the location, position, orientation, or coordinate of a position indicating element (e.g., sensor coils or other position indicating elements). This data may be stored in memory device 105 or other data storage location.

In some embodiments, software modules 211a-211n such as, for example, a display module, enable processor 203 to produce, format, or reformat one or more images from image space data, position/orientation/location data, or other data. Images produced from image space data, position/orientation/location data, other data, or any combination thereof may be displayed on a display device 215. In some embodiments, processor 203 displays one or more live images. Software modules 211a-211n such as, for example, the display module, may enable the generation and display of images of the anatomy of the patient with the position or orientation of a tracked instrument (e.g., any instrument having one or more position indicating elements thereupon) superimposed thereon in real time (such that motion of the tracked instrument within the anatomy of the patient is indicated on the superimposed images) for use in an image-guided procedure. In some embodiments, software modules 211a-211n such as, for example a display module, enables processor 203 to produce markings, lines, circles, spheres, letters, numbers or other indicators on an image of the anatomy of a patient. These markings may indicate features such as the boundaries of another image stored in memory device 205. In some embodiments, software modules 211a-211n such as, for example, a mapping module enables processor 203 to map a target lesion (e.g., a cancerous region) or other portion of a patient's anatomy or to perform other operations related to a map of the target lesion or portion of the patient's anatomy. In some embodiments, software modules 211a-211n such as, for example, display module generates and displays (e.g., on display device 215) the position of a puncture needle relative to a location in the target lesion, a projected path of the puncture needle including a path the puncture needle will follow if the puncture needle is extended past a distal end portion of the needle guide, a point at which the puncture needle will intersect the target lesion if the projected path of the puncture needle intersects the determined path of the target lesion, and an indicator of the closest approach from the puncture needle to the target lesion if the projected path of the puncture needle does not intersect tissue not intended to be treated or biopsied.

Display device 215 may include a computer monitor or other visual display device such as, for example, an LCD display, plasma screen display, cathode ray tube display, or other display device. Input device 217 may include a mouse, a stylus, a keyboard, a touchscreen interface (which may be associated with or integrated with display device 215), a voice activated input device (including a microphone and associated voice processing software), or other device wherein a user (e.g., a physician performing a prostate procedure or assistant thereto) can provide input to system 200 or its components.

Tracking device 221 may be operatively connected to computer element 201 via an input/output 213. In some embodiments, tracking device 221 need not be directly operatively connected to computer element 201, but data may be sent and received between tracking device 221 and computer element 201. Tracking device 221 may include an electromagnetic tracking device, global positioning system (GPS) enabled tracking device, an ultrasonic tracking device, a fiber-optic tracking device, an optical tracking device, radar tracking device, or other type of tracking device. Tracking device 221 may be used to obtain data regarding the three-dimensional location, position, coordinates, or other information regarding one or more position indicating elements within or around an anatomical region of the patient. Tracking device 221 may provide this data or information to computer element 201. In some embodiments, the position indicating elements tracked by tracking device 221, may be placed on or integrated in needle guide 225, biopsy needles (not shown), or other elements.

Imaging device 223 may include x-ray equipment, computerized tomography equipment, positron emission tomography equipment, magnetic resonance imaging equipment, fluoroscopy equipment, ultrasound equipment, an isocentric fluoroscopic device, a rotational fluoroscopic reconstruction system, a multislice computerized tomography device, an intravascular ultrasound imager, an optical coherence tomography (OCT) device, an optical imaging device, a single photon emission computed tomography device, a magnetic particle imaging device, or other imaging/scanning equipment.

Figure 3:
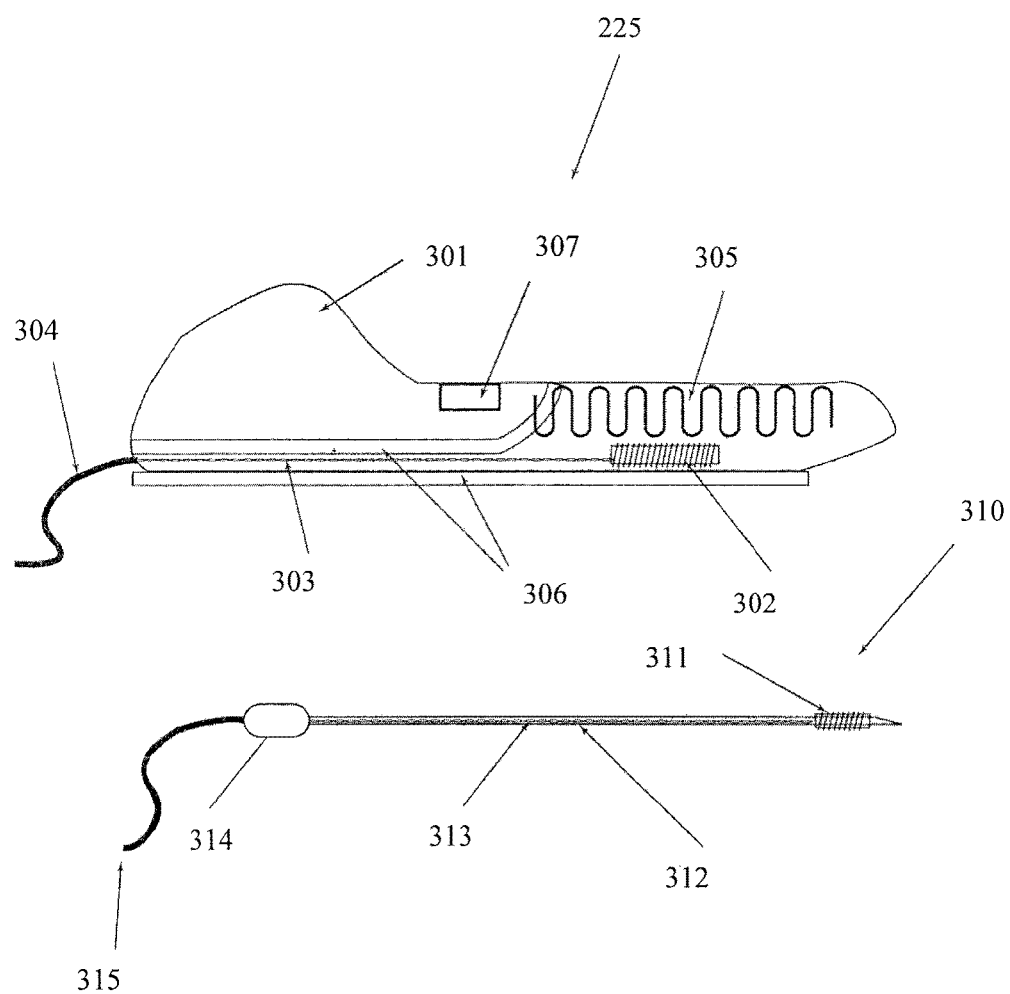
FIG. 3 is a perspective view of a needle assembly.

Referring now to FIG. 3, a detailed drawing of needle assembly 225 according to one embodiment is shown. Needle assembly may include a needle guide 301 and a biopsy or treatment needle 310.

Needle guide 301 may be adapted to be removable or permanently attached to an ultrasound transducer. Needle guide 301 may be formed from an elastomeric plastic such that it may be repeatedly snapped onto a transducer handle and held in place. In some embodiments, needle guide 301 may be manufactured using a combination of plastics and metallic elements to help retain it to the ultrasound transducer. Needle guide 301 may contain notches or other features to ensure repeatable mating of the needle guide 301 to a previously known position and orientation to the TRUS probe. Needle guide 301 may thus be repeatedly mounted relative to the scan planes of the transducer so that each time the needle guide 301 is attached to the TRUS probe, it is aligned in the same way.

Needle guide 301 may include a six degree of freedom position sensor 302 that may be adapted to determine the location and orientation of an ultrasound transducer in six degrees of freedom. In some embodiments, the position indicating elements are adapted to determine the location and orientation of one or more scan planes of an ultrasound transducer in a frame of reference. Position sensor 302 is connected by wire 303 to cable 304. Cable 304 is in turn connected to the position sensor. In embodiments, needle guide 301 may be disposable or reusable.

Needle guide 301 may include a cooling system 305 that can include, for example, a grid of tubes capable of transporting a cooling fluid such as chilled saline. These elements may serve to cool the rectal wall to prevent damage and reduce the chance of fistula formation during RF, microwave, laser or other thermal therapy of the prostate. In some configurations, needle guide 301 may include warming elements, also 305, that may serve to warm the rectal wall to prevent damage during cryotherapy. Instead of a chilled fluid, a warmed fluid is circulated. Such warming or cooling elements may be present on the superior wall of needle guide 301 in contact with the rectal wall that is directly adjacent to the prostate. In some configurations the warming and cooling elements may be incorporated directly into the ultrasound transducer.

Needle guide 301 may include one or more channels or lumens 306, for passage of a therapy or biopsy needle. In some embodiments, a plurality of parallel or oriented lumens 306 may be present on needle guide 301, two of which are indicated on the figure. This may facilitate the simultaneous or sequential introduction of multiple devices into the tissue to perform treatment, ablation, HDR, monitoring or biopsy etc. without moving the transducer. This could be used with a fixed position of ultrasound so that device positions could be predetermined and the probe not readjusted each time a new device is inserted. In some embodiments, the lumens 306 may be arranged as a cluster, pyramid, grid or other geometrical shape. In some embodiments, the position indicating elements may be adapted to determine the location of the lumen in needle guide 301 relative to the position indicating elements, i.e. the exit angle and location of these hollow tubes may be known relative to the origin of sensor 302. This may enable a needle to be introduced into tissue through needle guide 301 in a direction prescribed by the lumen in needle guide 301 known in advance from the position and orientation of the guide as determined by position sensor 302.

Needle guide 301 may include a temperature sensor 307 for measuring the temperature of for example, the rectal wall during a temperature altering therapy such as thermal ablation using laser, RF or microwave energy. Such temperature measuring elements may be present on the superior wall of needle guide 301 in contact with the rectal wall that is directly adjacent to the prostate or introduced as needles through one or more of lumens 306. Temperature sensor 307 may be a thermocouple thermistor or other temperature measurement devices.

While needle 310 is described herein as including a "biopsy needle", any other elongated instrument can be used. In some embodiments, needles may include sensors for the measurement of temperature, pressure, stiffness or some other property of the tissue into which the needle is introduced. The needles introduced through the needle guide may be configured to deliver radiofrequency energy, cryotherapy, microwave energy, IRE, laser or light energy, radioactive seeds for brachytherapy or other form of therapeutic energy.

Biopsy needle 310 may include a 5 or 6 degree of freedom position sensor 311 near the tip of its shaft 312. Wires 313 from sensor 311, if present, may run along or inside needle shaft 312 to a hub assembly 314 and to a cable 315 that attaches to position sensor 311. In some embodiments, the needle body portion of biopsy needle 301 may be, for example, 25 cm long with a 16 gauge (16 G) diameter. Other lengths or diameters may be used.

In cases where a spring-loaded biopsy "gun" type needle is used, the needle emanates an audible "click" when the biopsy gun trigger is pressed. The pressing of the trigger causes a rapid mechanical action that causes a needle or sleeve to be driven into the tissue, which is then captured by the gun. An example of a spring-loaded biopsy needle is the "Top Notch Automated Biopsy System" from Boston Scientific, Inc.

Figure 4:
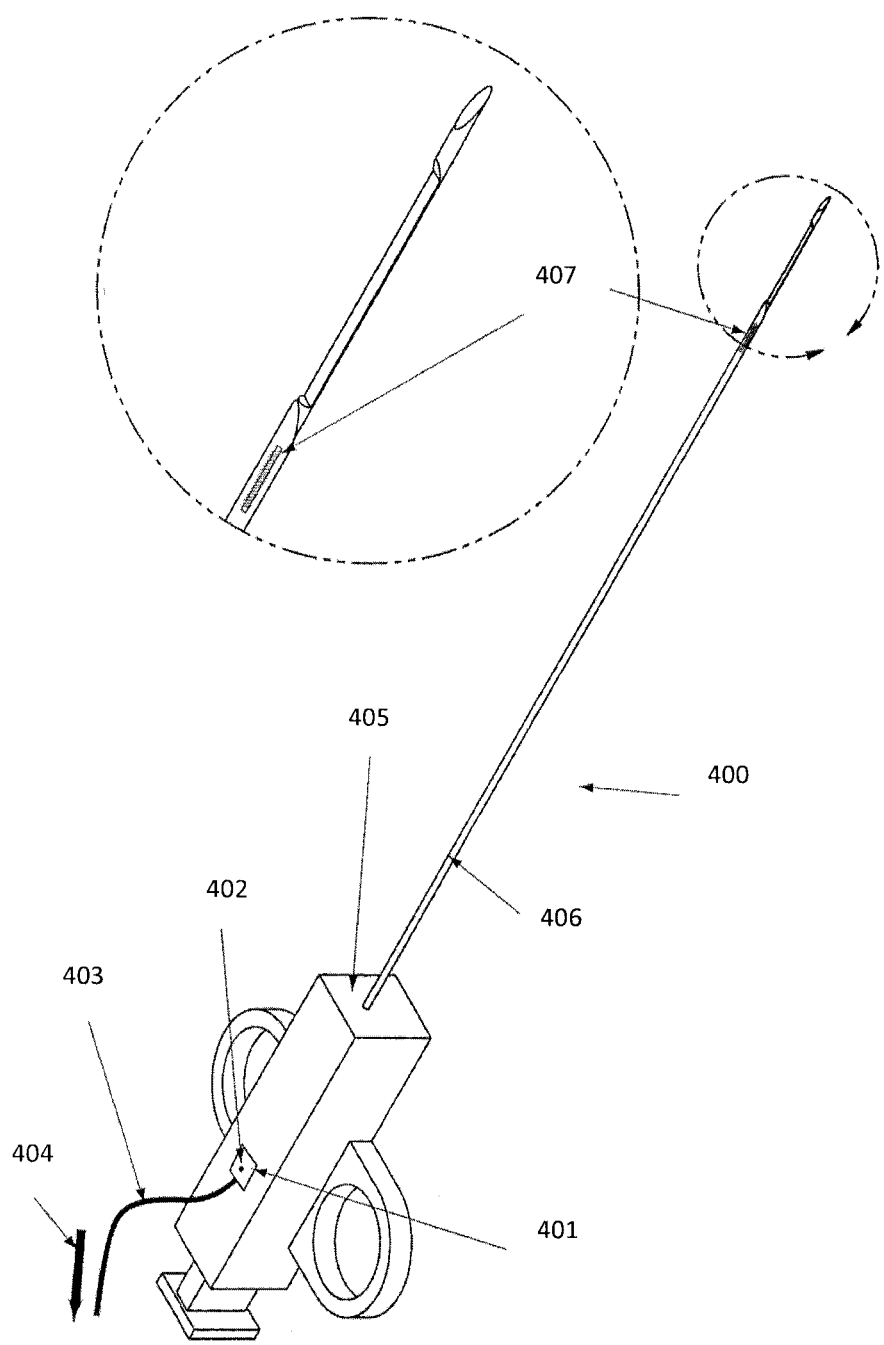
FIG. 4 is a perspective view of a biopsy gun equipped with a microphone containing a sound orifice.

In an embodiment shown in FIG. 4, a biopsy gun 400 is equipped with a microphone 401 containing a sound orifice 402. Microphone 401 may be for example a microelectromechanical system (MEMS) microphone, piezoelectric, carbon or other sound sensitive microphone that may be used to "listen" for the sound of the biopsy gun click. Sound may be conducted through signal cable 403 to a processor capable of receiving and interpreting signal 404, thereby triggering the correct sampling of the data and images. The microphone may be permanently or removably attached to biopsy needle handle 405 or within a portion of the biopsy needle's tubing 406. In some embodiments, cable 403 may also provide power or other signal pathways such as those from one or more position sensing elements 407, such as electromagnetic coils embedded in the biopsy device.

Figure 5:
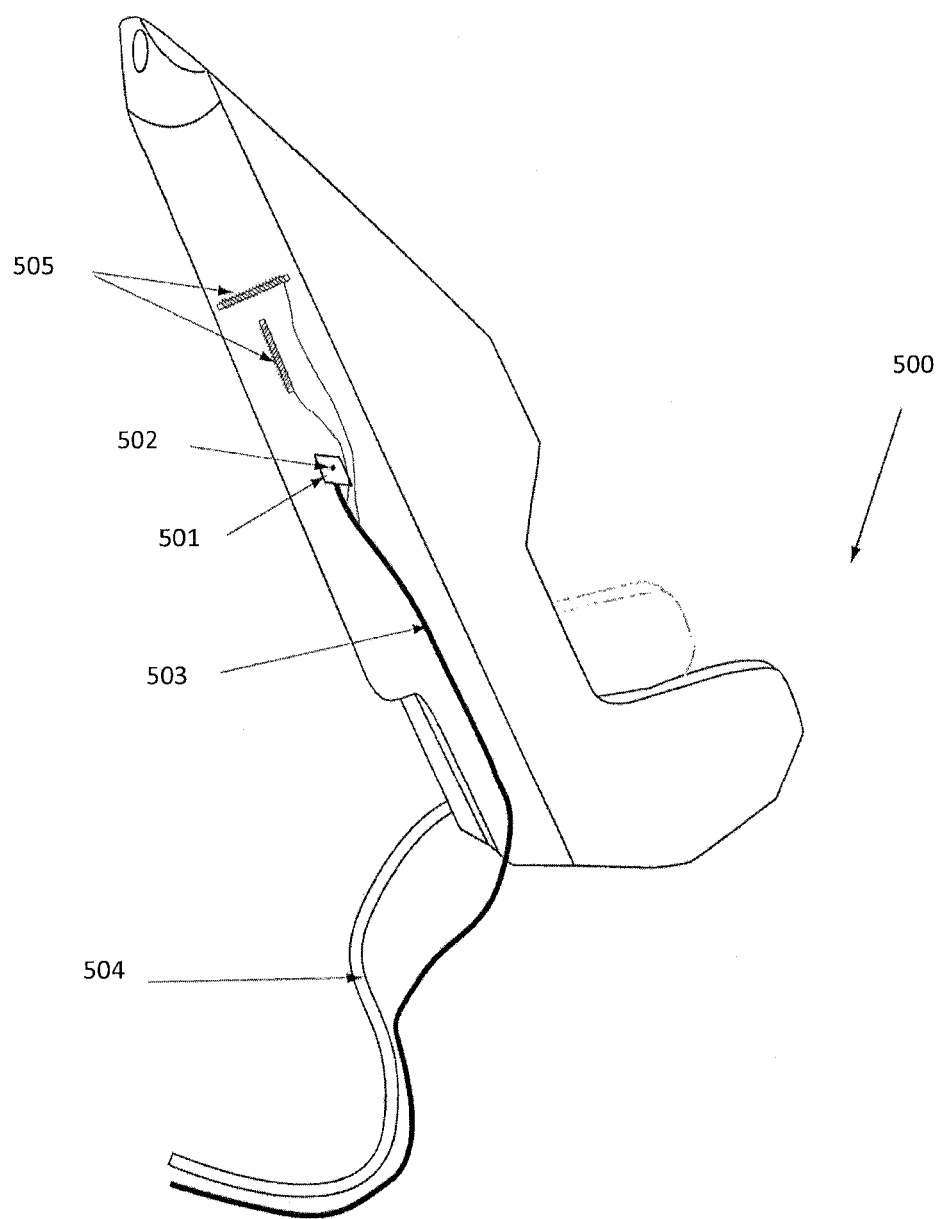
FIG. 5 is a perspective view of a needle guide.

In one embodiment as shown in FIG. 5, a microphone 501 may be permanently or removably attached to a needle guide 500. Needle guide 500 may be an endocavity needle guide used for transrectal ultrasound guided prostate biopsies. Needle guide 500 could be any type of needle guide commonly used to assist in performing biopsies including needle guides for abdominal or other ultrasound transducers, grid plates such as those commonly used in transperineal saturation biopsies, robotic needle guides, hand held cannulas, catheters, etc. Microphone 501 may contain a sound portal 502 and a signal or a combined signal-power cable 504. The needle guide may contain one or more position indicating elements such as electromagnetic sensing coils 505 together with the combined signal cable 504 for such coils, and microphone 501.

The microphone may be placed in the procedure room near the location of the biopsy, on the patient or in the vicinity of the procedure, or on another piece of apparatus in the room.

The microphone may be attached to an amplifier, buffer, isolation circuit, Schmitt-trigger, etc. to facilitate transfer of the trigger signal to a computer program or to aspects of the position sensor control unit that is being used to collect the data and video. An accelerometer or vibration detector may be substituted for the microphone. In an embodiment, the microphone, accelerometer, vibration detector or other device configured to detect the triggering of the biopsy device may be combined with position sensing elements to form an integrated unit as shown in FIGS. 4 and 5.

Figure 6:
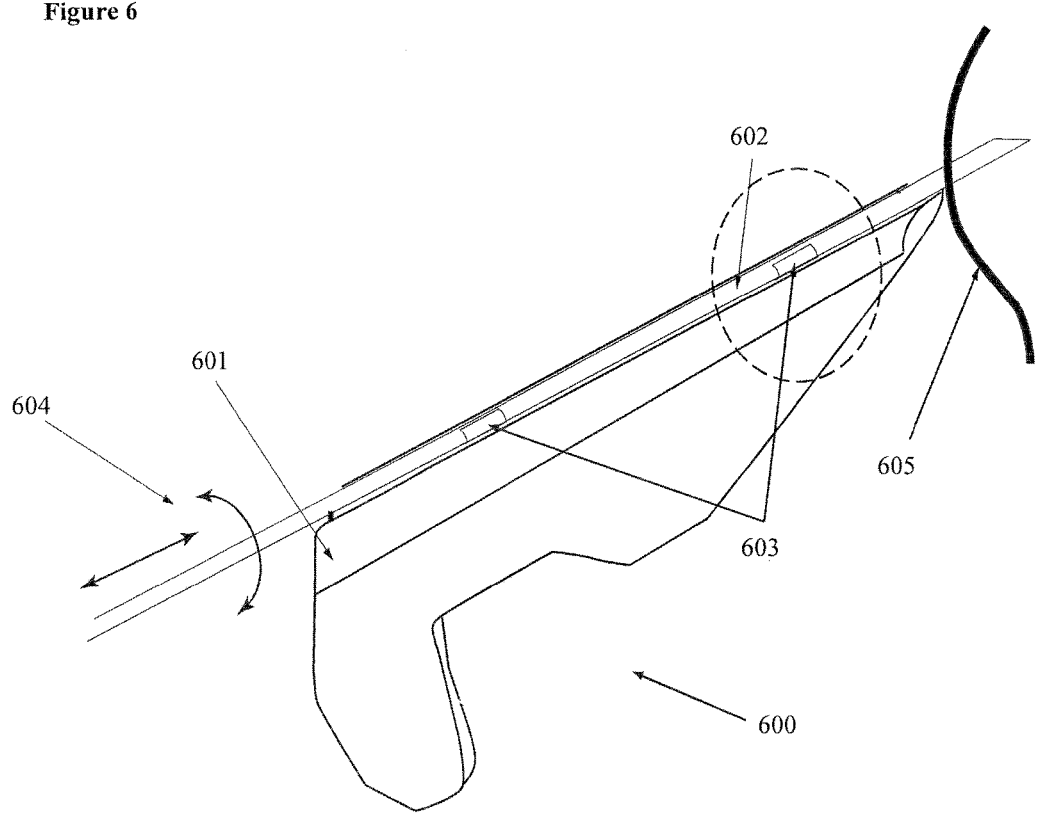
FIG. 6 is a perspective view of a needle guide.

Turning to FIG. 6, another embodiment of a needle guide is shown. Needle guide 600 may be removably and repeatably attached to an ultrasound transducer such as a TRUS probe (not shown). Needle guide 600 includes a housing 601 onto which a needle 602, such as a biopsy or therapeutic needle, may be placed. Needle 602 may be removably retained by retaining feature 603 which may be moved to retain or release needle 602. In the retained position, retaining feature 603 restrain needle 602 from moving or being rotated, with the exception of the axial translation and axial rotation indicated by arrows 604. In the released position (not shown on this figure), needle 602 may be completely removed from needle guide 600. Retaining feature 603, once released, enables needle 602 to be completely removed from needle guide 600 even when inserted into tissue 605 without necessitating sliding of needle 602 though needle guide 600.

Figures 7, 7A, 7B, 7C:
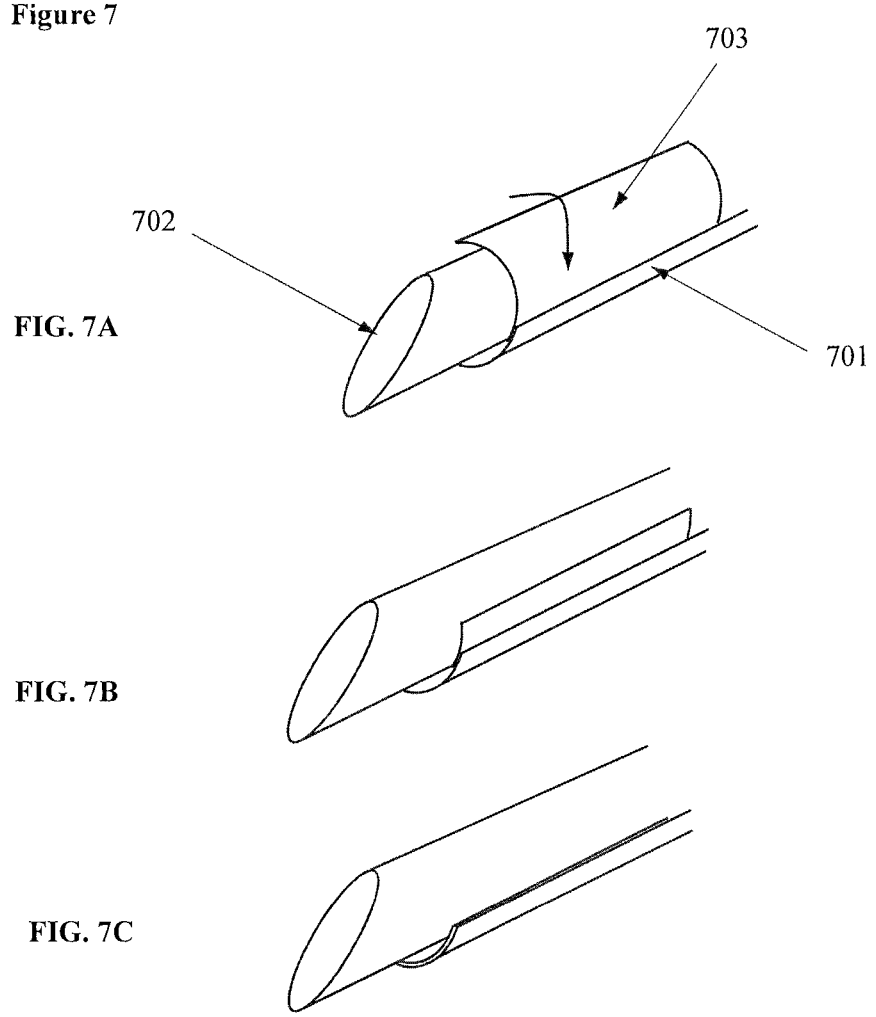
FIG. 7A-C is a close-up view of a retaining feature on a needle guide.

FIG. 7 shows a close-up view of the area within the dotted circle in FIG. 6. An embodiment of a retaining feature 703 is shown. Needle 702 rests on a portion of needle guide 701. In a closed position, needle 702 is retained by retaining feature 703. If as indicated by the arrow in FIG. 7A, retaining feature 703 is rotated, needle 702 becomes less constrained as shown in FIGS. 7B and 7C. In FIG. 7C, retaining feature 703 is positioned such that needle 702 is free to be removed from needle guide 701.

Figures 8, 8A, 8B, 8C:
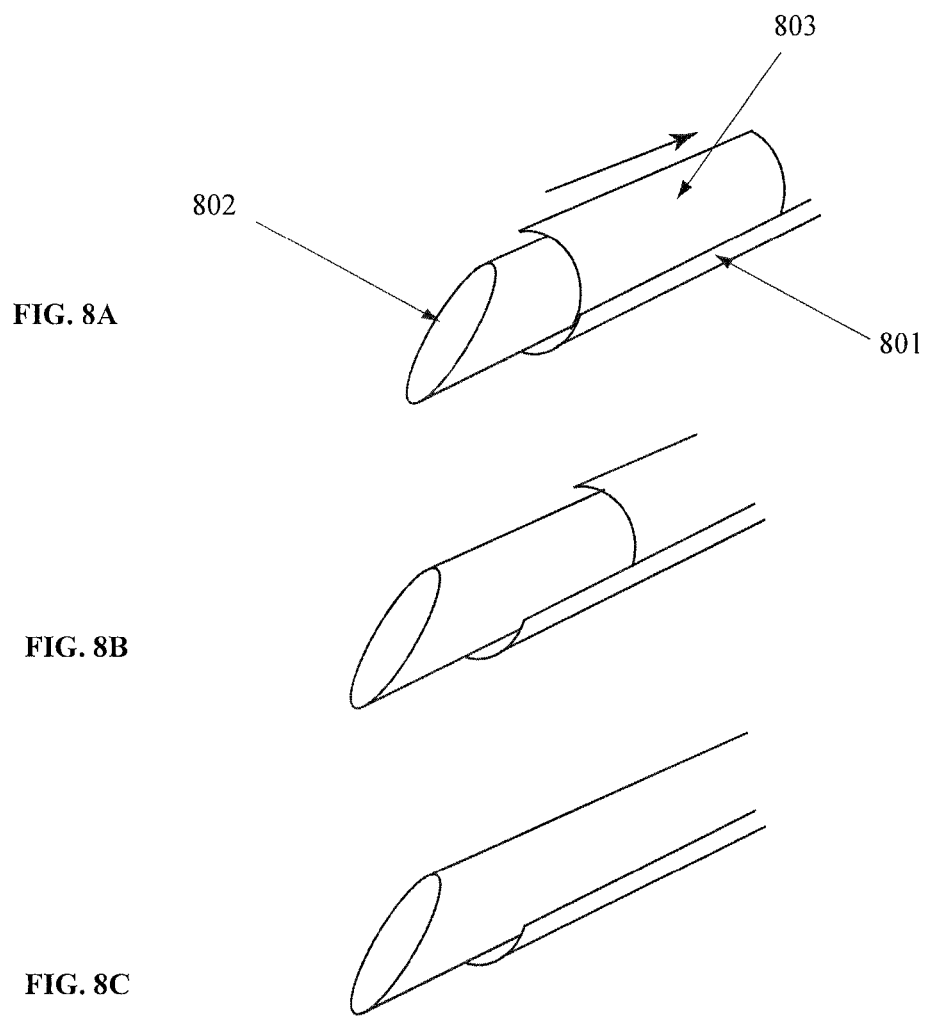
FIG. 8A-C is a close-up view of a retaining feature on a needle guide.

FIG. 8 shows another embodiment of a retaining feature 803. Retaining feature 803 uses a sliding mechanism. Retaining feature 803 may be slid in the direction shown in FIG. 8A from a location that retains needle 802, to an intermediate location shown in FIG. 8B where needle 802 becomes less constrained. Retaining feature 803 is eventually completely removed as shown in FIG. 8C, thus freeing needle 802.

In an embodiment, retaining feature may be a single, multiple, or multiple but connected feature. In an embodiment, the retaining feature may be attached with a handle to facilitate the motion of the feature. In an embodiment, the moving portion of the constraining mechanism may be substituted with a series of tabs or other features that allow unconstraining of a functional needle.

Figure 9:
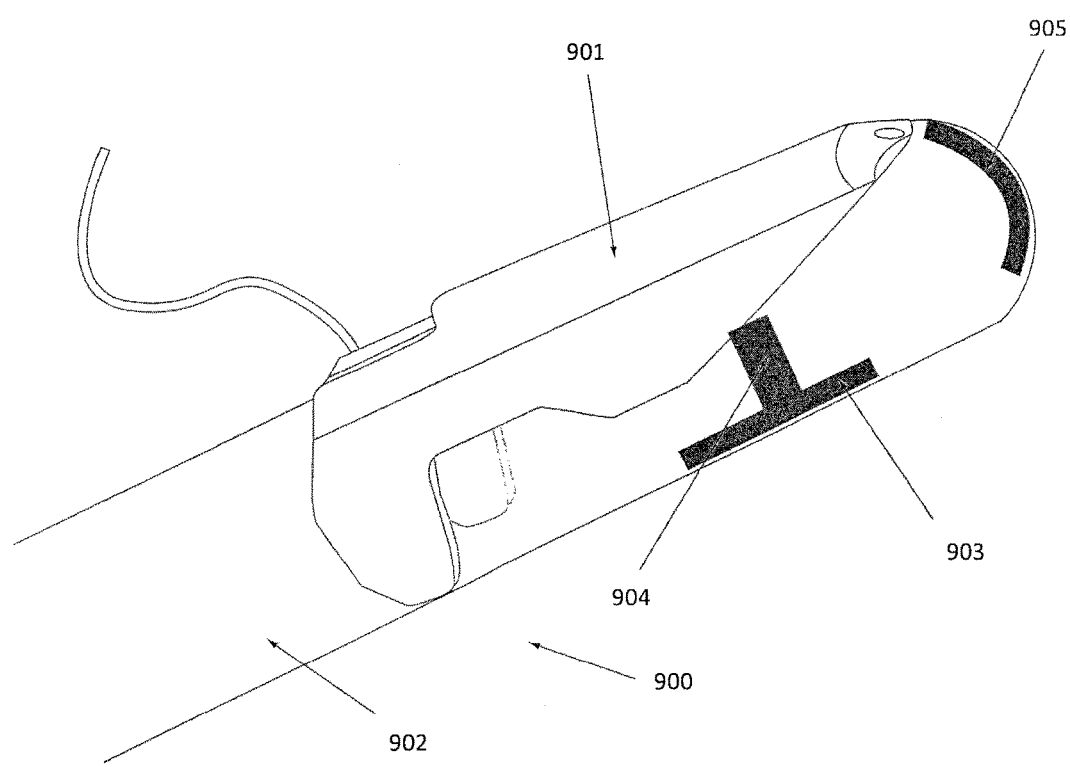
FIG. 9 is a perspective view of a needle guide assembly mounted on the end of a triplane transducer.

In an embodiment, a needle guide may be attached to a TRUS transducer. The ultrasound transducer may be capable of imaging one or more planes simultaneously. For example, a biplane probe may image two roughly perpendicular planes enabling two image "slices" to be obtained through the prostate gland at the same time. In a tri-planar probe, three images may be obtained. The transducer may also be used to image only a single plane, although that would require a slightly altered method. FIG. 9 shows the end of a triplane transducer/needle guide assembly 900 according to one embodiment. Needle guide 901 is shown attached to a transducer 902. The transducer includes three separate scan planes shown as a sagittal transducer 903, an axial transducer 904, and an endfire transducer 905. While the ultrasound probe tracker is described herein as including a needle guide, a sleeve or specially designed ultrasound transducer or other device may embody many or all of the features ascribed to the needle guide. Similarly, other living imaging modalities may include trackers tuned to their specific requirements, e.g. an endoscope tracker or a fluoroscope tracker.

Figure 10:
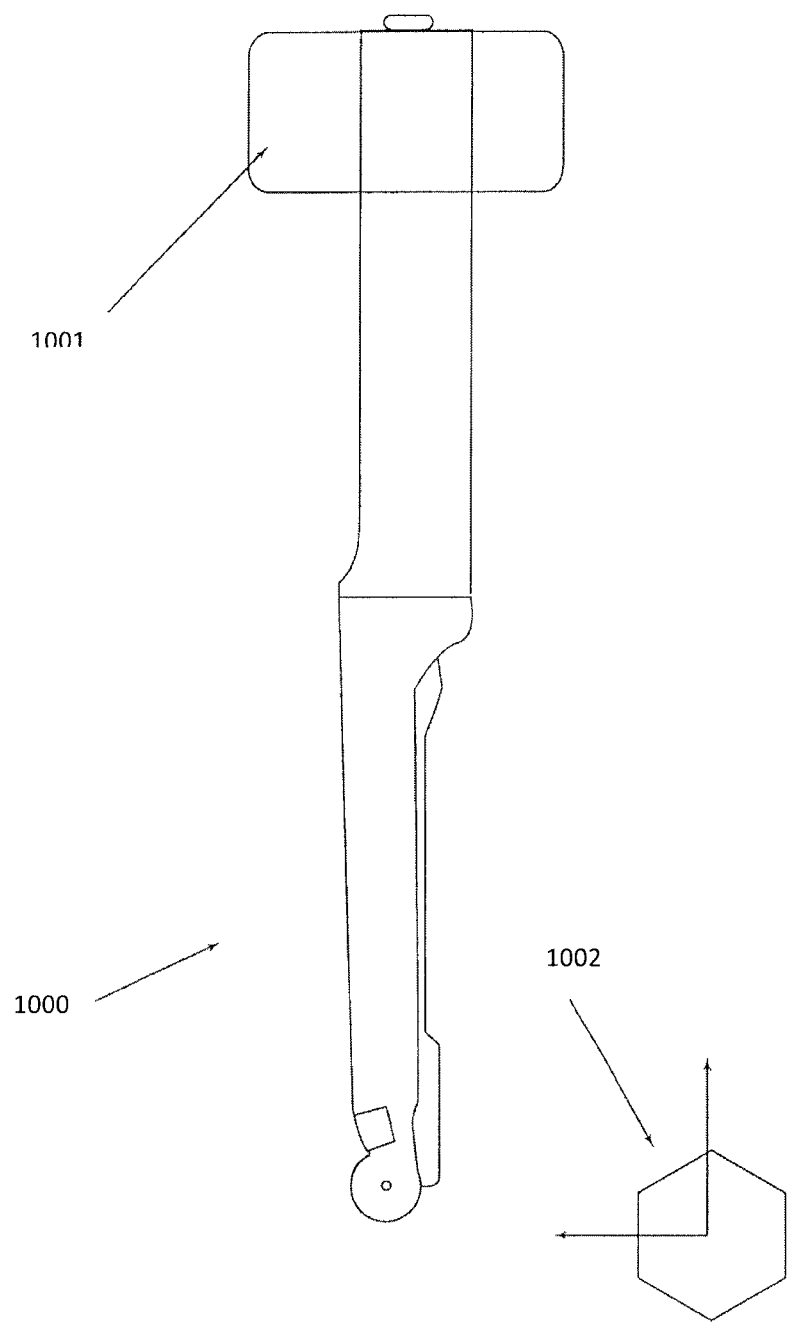
FIG. 10 is a view of a TRUS probe having a field generator.

A TRUS probe 1000 itself may have a field generator 1001 fixed either removably or permanently to it as indicated in the embodiment shown in FIG. 10. Normally the field generator has associated with it a frame of reference or coordinate system, i.e. patient space. In the case of the field generator located on the transducer handle as shown, an external six degree-of-freedom reference tracker 1002 must be used as the origin of the patient space. Such a tracker may be placed on, or in the patient, or on a structure such as the patient table. The reference tracker 1002 may be removably fixed, for example inside a Foley catheter that is placed in the patient. Alternatively a purpose built Foley catheter containing an integrated tracker can be used. Because a Foley catheter is placed through the urethra that passes through the prostate and fixed in place near the prostate, the placement of the reference in the catheter or purpose building a catheter for this use would additionally serve to dynamically reference the prostate and account for motion therein during the procedure. The Foley catheter may have additional lumens, for example, for cooling the urethra or other functions.

Figure 11:
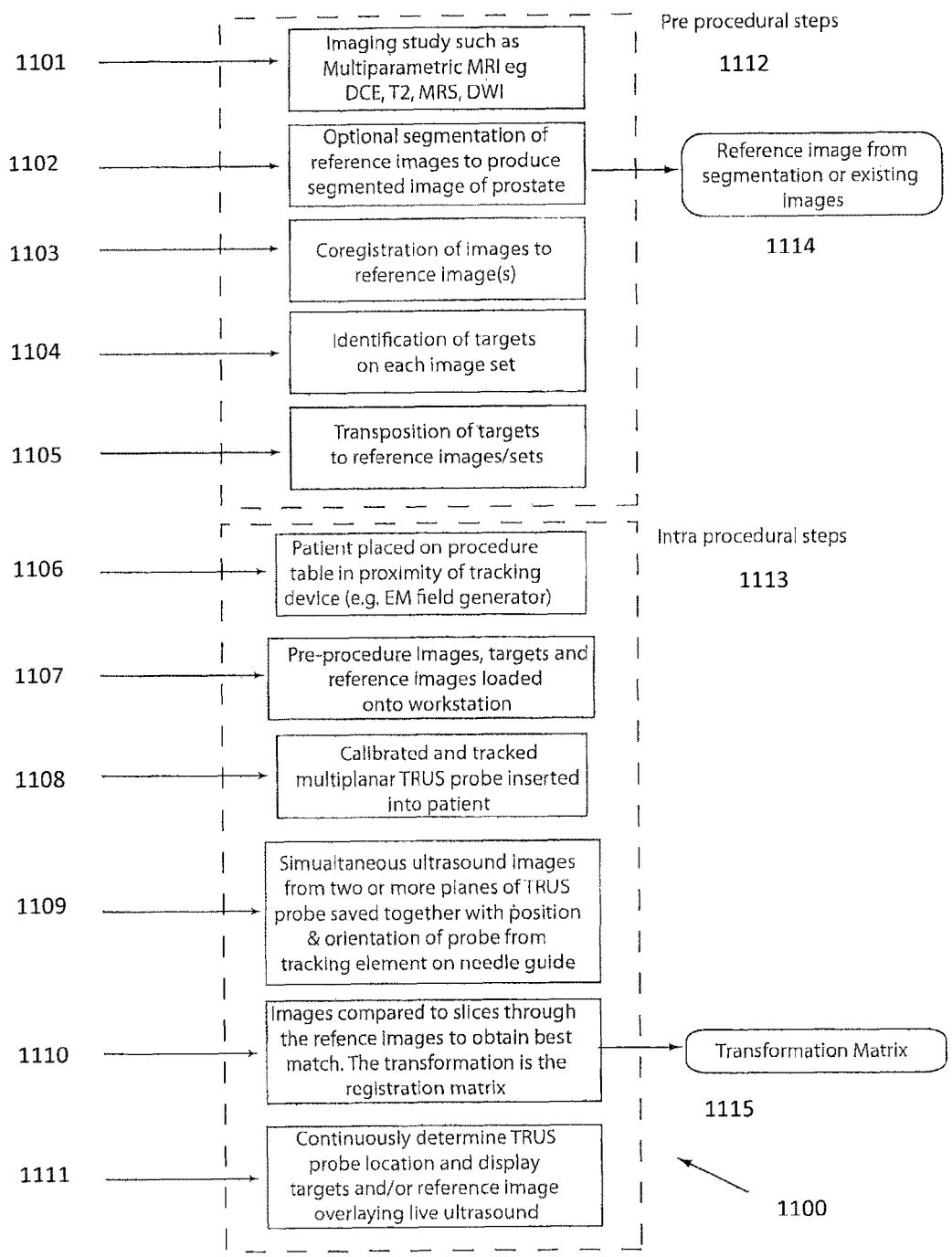
FIG. 11 is a flowchart showing a method for prostate diagnosis and intervention according to an embodiment.

In FIG. 11, flowchart 1100 indicates a workflow for a method of using embodiments of the invention. The workflow is divided into pre-operative procedures 1112 and intra-operative procedures 1113. In the pre-operative procedures portion of the workflow, one or more volumetric imaging studies 1101 are first performed. Such imaging study may consist of a multiparametric MRI or other imaging study in which lesions of the prostate are visible including studies using magnetic resonance imaging, computed tomography, cone beam CT, positron emission tomography, ultrasound, ultrasound elastography, contrast enhanced US (CEUS), or magnetic particle imaging.

In 1102, the one or more volumetric study may be segmented to produce an outline, mesh or solid model of the prostate 1114. This may be done using manual or automatic methods that are known in the art. In an embodiment, the segmentation may occur on the T2 weighted MRI image set, or any other image set that clearly delineates the boundaries and features of the prostate. Being created from one or more of the volumetric image sets, the segmented images 1114 may also be registered to the reference images.

In 1103, the one or more volumetric image sets obtained in 1101 can be co-registered to a single image set, i.e., the reference images. In an embodiment, the reference images may be the T2 weighted MRI image set, the segmented images 1114, or any other volumetric data set. Co-registration of images may be done using a variety of techniques including manual overlay, as well as automatic or semi-automatic methods such as intensity based methods, texture based methods, feature based methods, etc. Once co-registered, any features identified on one image set may be mapped to one of the co-registered images and displayed on it if desired. For example a feature identified on a diffusion weighted image set may be mapped to the T2 data set or vice versa.

In some cases, some of the volumetric images obtained in 1101 may be acquired in the same frame of reference, i.e. they are co-registered to begin with. This may be the case of MRI scans which are sometimes acquired simultaneously. In the case that the images are not acquired simultaneously but the images sets are translated, scaled or rotated relative to one another in three-dimensional space, then a registration procedure as known in the art must be determined. Some algorithmic methods to perform the registration include singular valued decomposition or iterative closest points in which three or more corresponding features are located on the images sets to be registered. Typically a 4×4 transformation matrix is calculated that maps the images from one coordinate system into the coordinate system of the reference images.

The reference images may also be a segmented version of one or more of the image sets, e.g. images 1114 or some other segmented images. In this embodiment, the reference images may be vastly simplified representations of the key MRI data, for example the surface of the prostate, with or without the path of the urethra or other salient features marked. In an embodiment, the reference images may include more than one type of reference image, for example the T2 plus the segmented images. This may be done by first co-registering the different image sets, for example the T2, MRS, DWI and DCE, and transposing the coordinates and/or target shape identified on the different image data sets to the reference images, for example the T2 or segmented images.

In 1104, the candidate lesions or targets are identified on some or all of the image sets acquired in 1101. These may include potential lesions as well as structures of interest in the images. The targets may be segmented tumors or locations corresponding to the center point or other point of interest in a tumor. In an embodiment, multiparametric MRI may be used in which, for example, T2 weighted images, dynamic contrast enhanced (DCE) MR images, MR spectroscopic (MRS) data and diffusion weighted MR imaging (DWI) may be examined to determine the location of possible cancer tumors. In a similar way, other imaging modalities and combination of modalities may be used to determine the location of possible cancers within the prostate. 3D ultrasound elastography or contrast enhanced ultrasound (CEUS) may be used to locate potential targets.

Because the registration between images is known from 1103, the targets identified on any of the images acquired in 1101 can be transposed to and shown on the reference images or on the segmented images as indicated in 1105. Transposing targets from multiple images onto one or more reference images is advantageous because it limits the amount of data that must be viewed by the physician during the procedure. In an embodiment, the candidate lesions may be indicated as dots or "blobs" in a bright color to be displayed concomitantly with the reference images. In some embodiments the different image sets may be pre-registered at the time of the scans. In this way, targets present in one of the alternate image sets but not on the reference images are mapped to or made visible on the reference images. Targets present on any of the individual scans are collectively mapped to and may be displayed on the reference images in this way.

The reference images may be saved together with the targets for later use during a procedure designed to biopsy, selectively ablate or otherwise sample or treat the targets.

This data may collectively constitute a plan. In an embodiment, the plan data are used during an interventional procedure that is designed to target the targets identified on the plan.

Next the intra-operative procedures 1113 will be considered. These take place at the time of the intervention of the patient. The procedures may be performed at a different time than the planning or pre-procedure steps described above. During 1106, the patient is placed on the procedure table and a tracking device such as an electromagnetic field generator may be placed under or in close proximity to the patient. If a field generator is present on the handle of the transducer as described above, then the reference tracker is placed in or on the patient or table as described above.

In 1107, the images which may include the reference images, targets and segmented volume are available and may be loaded onto the computer system used for the intra-procedural portion of the workflow. Not all image sets need to be loaded as not all may be required depending on the procedure. For example, some of the reference images in the form of the original MRI scans may not be needed, and not loaded onto the workstation. Likewise some of the other scans may not be needed and remain unloaded.

Prior to use, the needle guide containing a position sensor (if the probe does not already contain integrated position sensor) may be placed onto the ultrasound and the system calibrated to relate the coordinate system fixed to the tracker to the coordinate system of the scan plane of the ultrasound. Many methods of calibration exist, some of which are summarized in the document "3D ULTRASOUND PROBE CALIBRATION WITHOUT A POSITION SENSOR", by A. H. Gee, N. E. Houghton, G. M. Treece and R. W. Prager, CUED/F-INFENG/TR 488 September 2004 (Cambridge University, Department of Engineering, Trumpington Street, Cambridge CB2 1PZ, United Kingdom) and in the document "Probe Calibration for Freehand 3-D Ultrasound", by F. Lindseth, G. A. Tangen, T. Langø, and J. Bang, Ultrasound in Medicine and Biology, 29(11): 1607-1623, November 2003. Once calibration has been completed, any position (u,v) on the ultrasound display may be combined with the calibration obtained and the coordinates of the needle guide to describe the location of the point in the patient space. The locations of the scan plans are also known in patient space as the ultrasound is moved and its location reported by the tracking device.

In 1108, the TRUS probe equipped with the needle guide is inserted into the patient to allow viewing of the prostate gland. The images from the ultrasound system are relayed to the computer system on which the pre-procedure images and targets reside. When the images are obtained, the location of the scan planes may be recorded using a tracking device and position indicating elements placed on a needle guide or probe itself. Because the probe is tracked and its location is known in patient space, the location of the ultrasound scan planes is also known in patient space and it is possible to determine from any coordinate (u,v) on the ultrasound image, the location (x, y, z) that the point represents in patient space.

Figure 12:
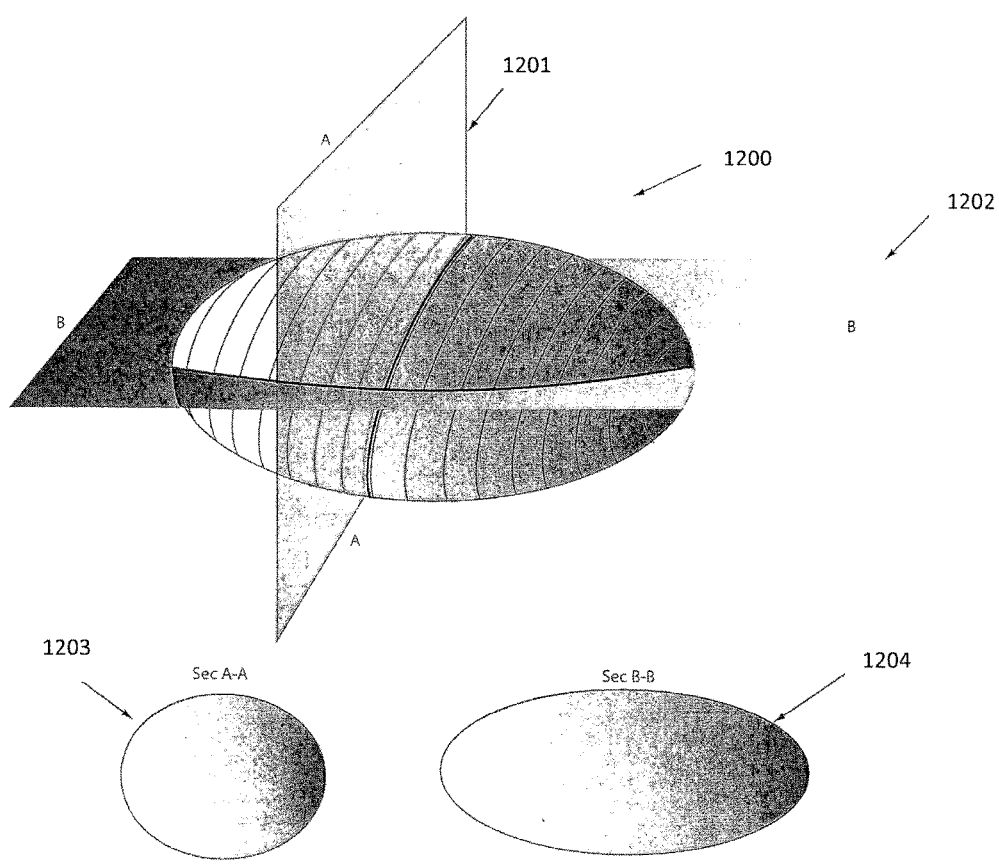
FIG. 12 is a simplified representation of sections of a prostate obtained using a biplane ultrasound probe.

In 1109, two or more ultrasound views obtained from the multiplanar ultrasound are captured on the computer system along with the location and orientation of the probe in patient space. In FIG. 12, two such sections obtained are depicted in a simplified way. The prostate 1200 is scanned using a biplane ultrasound probe in this example. The ultrasound probe may produce two scan planes 1201 and 1202 that appear as more or less perpendicular sections through the prostate as depicted in 1203 and 1204. These sections together with the location and orientation of the probe are recorded and from the calibration it is then possible to know every location in the images 1203 and 1204 in patient space. In an embodiment, scan planes 1201 and 1202 are produced by manually rotating a single plane ultrasound. In an embodiment, multiple scan planes may be likewise produced by manually or automatically sweeping the scan plane (for example using a mechanism to "wobble" the ultrasound transducer crystal or by using a phased array ultrasound) in a linear or rotational fashion or combination thereof.

Returning to FIG. 11, the prostate had been segmented in 1102 in MR image space so that a mesh or solid model of the prostate is available. This enables it to be mathematically sectioned in any orientation. If the prostate also is segmented from the captured ultrasound images, two or more contours outlining the prostate in patient space for the captured images are also available. It is then possible to perform a search of the prostate obtained from the pre-procedure model of the prostate with the intraprocedure images of the prostate as indicated in 1114 since the relative orientations and positions of the scan planes are known relative to one another. The contours can be checked against the model of the prostate by performing an exhaustive search to find the best matching contours to cross sections of the segmentation.

Such a procedure is also possible using multiplanar reformats of T2 images for example. In that case, texture or feature matching or other algorithms may be used. It may be necessary to synthesize ultrasound-like images from the MRI to efficiently match the images. Such a technique for CT images was described by R. Shams, R. Hartley, and N. Navab in Med Image Comput Comput Assist Interv. 2008; 11(Pt 2):734-41 in the article entitled "Real-time simulation of medical ultrasound from CT Images" and a similar procedure is possible using MRI images as source images.

Cross sections of the mesh or solid model of the prostate may be systematically generated by the computer at different slice orientations and locations until the best match is found of the two or more ultrasound slices in 1110. The spatial relationship of the two or more planes may be used to assist in the search for the best fit. A search technique that uses a combination of coarse increments and small scale adjustments may be used to perform the search. The search algorithm may be made more efficient from some a priori knowledge of the approximate position and orientation of the prostate relative to the probe especially if it is first approximately aligned within a pre-specified window that the user is instructed to place the probe into. For example, the user may be instructed to image the prostate approximately so that the tip of the image is aligned with a pre-marked line, and the left edge is in a particular location.

Once the optimal slices through the mesh or solid model are determined, the orientation and location of the slices may be determined in image space. The transformation required to match the cross sectional slice from the ultrasound in patient space to that of image space is calculated. This matrix is the registration matrix 1115 and may be represented by a 4×4 matrix. This registration matrix encodes a rotational and translational mapping from the patient space represented by the needle guide location and orientation expressed in the coordinate system of the tracking device to the image space in which the targets have been marked. In this way, it is possible to transform the locations of the targets into patient space.

Once registered, targets that were located in the reference image set can be displayed on the live ultrasound by first applying the transformation matrix and if the current scan slices are sufficiently close to one of the targets, it can be displayed 1111. Likewise, a contour representing the cross section through the prostate may be generated from the segmented mesh or volume or a multi planar reformat may be calculated from the MRI data.

Overlaying contours corresponding to the segmented prostate on top of the ultrasound images may be used to confirm to the user that the MRI and TRUS are in registration. If the outline of the prostate as determined by the MRI does not reasonably overlap the edges of the prostate from the TRUS, then it may be necessary to reregister the two scans. It is possible to repeat the registration as often as required to account for deformation or patient motion.

In an embodiment, the MRI may be reformatted to multiplanar reformats (MPR) views through the prostate that correspond to those displayed by the ultrasound. In this way the images may be fused to show a combined image that has features of both the TRUS and the MRI. In an embodiment, the MPR may be of the segmented prostate so that lines and features present in the segmentation may be viewed simultaneously to the ultrasound.

Since the relationship between any ultrasound plane is known, the targets or cross sectional data may be displayed on any plane. So for example, in a triplanar probe, the sagittal and axial planes may be used for registration but then the endfire plane may be used for targeting.

Once the target location has been converted from image space into patient space, it is possible to target the lesion using position indicating elements to assist in locating the needle or probe in the appropriate target.

In an embodiment, a position indicating element is placed onto the tip of a biopsy or therapy needle or cannula so that it can be directed into the target through, for example, the perineum. In an embodiment, the needle guide is equipped with lumens. The orientation and location of the lumens is known relative to the position indicating element of the needle guide. The path of a treatment or biopsy needle placed in the lumen can therefore be calculated and displayed relative to one or more of the targets. The needle guide is then directed so that the needle placed in the lumen of the needle guide is made to intersect the target. Any needle inserted into the needle guide could then be used to biopsy or treat the lesion transrectally.

In an embodiment the path of any needle introduced into a lumen of the needle guide may be overlaid on top of the live images from the ultrasound as a graphical icon such as a line. In an embodiment, the live images, the needle path and the targets may all be displayed simultaneously.

In an embodiment, the needle introduced into the lumen may be made to vibrate at a frequency that causes features in the prostate to become more visible under ultrasound. In an embodiment, a device introduced into the urethra can be made to vibrate at a frequency that renders features such as tumors more visible under ultrasound.

Figure 13:
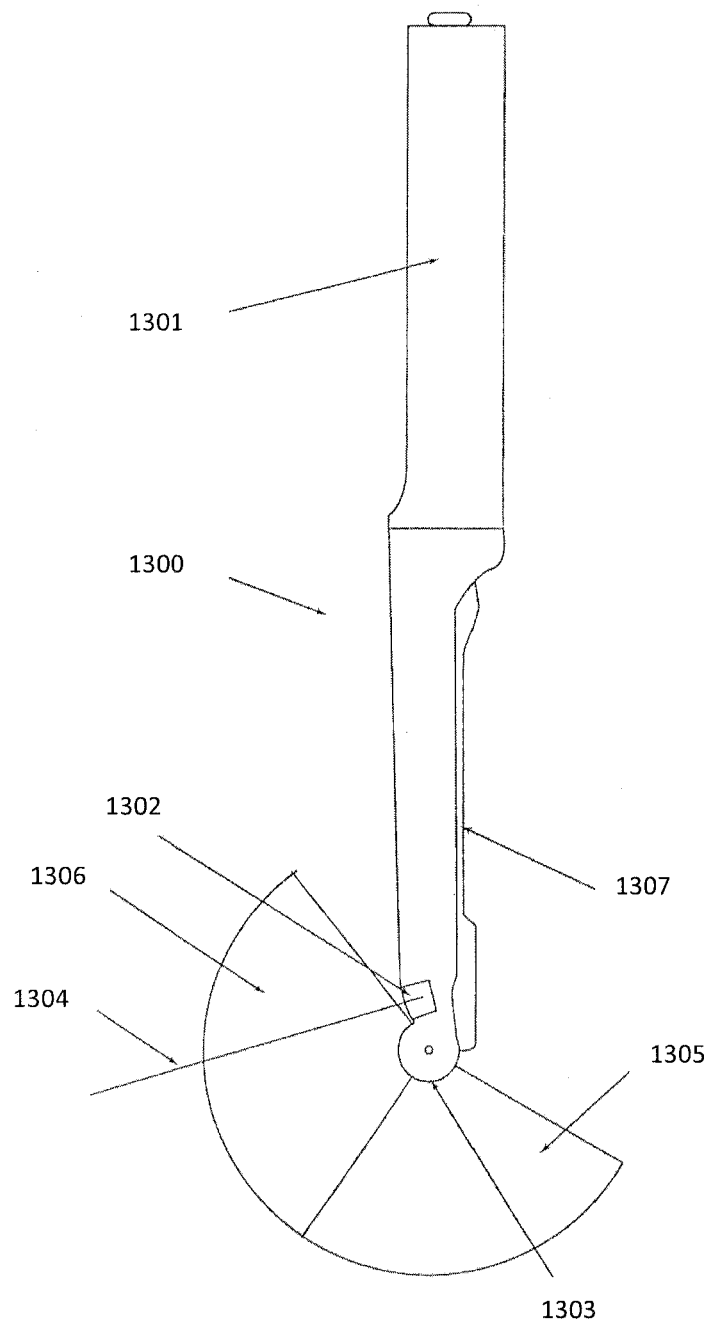
FIG. 13 is a view of a triplanar probe.

A probe showing an embodiment of a triplanar probe produced by BK medical (Herlev, Denmark), the 8818 triplanar probe, is shown in FIG. 13. The probe system 1300 is comprised of a handle 1301 and two ultrasound arrays 1302 and 1303. Array 1302 images the prostate axially while array 1303 images sagittally. The array 1302 produces an image plane that is indicated by 1304 which is into the plane of the paper. Array 1303 produces an image plane consisting of two planes, 1305 and 1306, which are the same plane but spilt. This provides the true sagittal plane 1306, together with an endfire plane 1305. The endfire is the same plane as the sagittal plane but the sector of the circle is pointed at the end. Details of a similar probe are also available in U.S. patent application Ser. No. 12/225,488, "Ultrasound Probe" by Nygaard, Karlsson, Fortling and Sorensen.

All documents cited in the Specification are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A needle guide for use during a procedure, the needle guide comprising:
 a housing;
 at least one channel that extends the length of the housing along a longitudinal direction of the housing, the at least one channel for receiving a needle device for use during a procedure; and
 a curved retaining mechanism for releasably securing the needle device in the at least one channel of the housing, the curved retaining mechanism rotatable about a longitudinal axis of the at least one channel from a retaining position to a released position, wherein the retaining position enables the needle device to be retained in the at least one channel and capable of axial translation and rotation, and wherein the released position enables the needle device to be released from the at least one channel without necessitating sliding of the needle device through the at least one channel.

2. The needle guide of claim 1, further comprising a temperature measurement device.

3. The needle guide of claim 1, further comprising a cooling system or a warming system.

4. The needle guide of claim 1, further comprising a position sensor.

5. The needle guide of claim 4, wherein the position sensor is a six-degree of freedom position sensor.

6. The needle guide of claim 1, wherein the at least one channel further comprises a plurality of channels to enable the introduction of multiple devices during the procedure.

7. The needle guide of claim 1, further comprising a device for determining when a biopsy gun has been fired, the device selected from the group consisting of a microphone, an accelerometer, and a vibration detector.

8. The needle guide of claim 1, further comprising a microphone removably attached to the housing.

9. The needle guide of claim 1, further comprising:
 a six-degree of freedom position sensor;
 a temperature sensor; and
 one or more warming elements.

10. A system for performing image-guided procedures, the system comprising:
 a needle device;
 a needle guide, comprising:
  (i) a housing;
  (ii) at least one channel that extends the length of the housing along a longitudinal direction of the housing, the at least one channel for receiving the needle device for use during a procedure; and (iii) a curved retaining mechanism for releasably securing the needle device in the at least one channel of the housing, the curved retaining mechanism rotatable about a longitudinal axis of the at least one channel from a retaining position to a released position, wherein the retaining position enables the needle device to be retained in the at least one channel and capable of axial translation and rotation, and wherein the released position enables the needle device to be released from the at least one channel without necessitating sliding of the needle device through the at least one channel; and a tracking device.

11. The system of claim 10, further comprising:
an imaging device selected from the group consisting of an x-ray equipment, a computerized tomography equipment, a positron emission tomography equipment, a magnetic resonance imaging equipment, a fluoroscopy equipment, an ultrasound equipment, an isocentric fluoroscopic device, a rotational fluoroscopic reconstruction system, a multislice computerized tomography device, an intravascular ultrasound imager, an optical coherence tomography (OCT) device, an optical imaging device, a single photon emission computed tomography device, and a magnetic particle imaging device.

12. The system of claim 10, wherein the tracking device is selected from the group consisting of an electromagnetic tracking device, a global positioning system (GPS) enabled tracking device, an ultrasonic tracking device, a fiber-optic tracking device, an optical tracking device, and a radar tracking device.

13. The system of claim 10, wherein the needle device comprises a position sensor.

14. The system of claim 10, wherein the needle device comprises a microphone, an accelerometer, or a vibration detector.

15. The system of claim 10, wherein the needle guide further comprises a six-degree of freedom position sensor.

16. The system of claim 10, wherein the needle guide further comprises a device for determining when a biopsy gun has been fired, the device selected from the group consisting of a microphone, an accelerometer, and a vibration detector.

17. The system of claim 10, wherein the at least one channel further comprises a plurality of channels to enable the introduction of multiple devices during the procedure.

18. The system of claim 10, wherein the needle device comprises a biopsy needle or a treatment needle.

19. The system of claim 10, further comprising:
an ultrasound transducer.

20. The system of claim 19, wherein the needle guide is removably coupled to the ultrasound transducer.

21. The system of claim 19, wherein the ultrasound transducer comprises a Transrectal Ultrasonography (TRUS) probe.

22. The system of claim 10, wherein the needle guide further comprises:
a temperature sensor.

23. The system of claim 10, wherein the needle guide further comprises:
a temperature sensor; and
one or more warming elements.

24. The system of claim 10, wherein the needle guide further comprises:
a temperature sensor; and
a cooling system.

* * * * *